US00PP09892P

United States Patent [19]

Glicenstein

[11] Patent Number: Plant 9,892

[45] Date of Patent: May 13, 1997

[54] CHRYSANTHEMUM PLANT NAMED 'FOXY VALERIE'

[75] Inventor: Leon Glicenstein, Salinas, Calif.

[73] Assignee: Yoder Brothers, Inc., Barberton, Ohio

[21] Appl. No.: 606,036

[22] Filed: Feb. 22, 1996

[51] Int. Cl.[6] ..... A01H 5/00

[52] U.S. Cl. ..... Plt./82

[58] Field of Search ..... Plt./76, 82

[56] References Cited

U.S. PATENT DOCUMENTS

P.P. 8,985 11/1994 VandenBerg ..... Plt./76
4,616,099 10/1986 Sparkes ..... 47/58

OTHER PUBLICATIONS

Broertjes, et al., 1980, "A Mutant of a Mutant of a . . . Irradiation of Progressive Radiation—induced Mutants in a Mutation Breeding Programme with *Chrysanthemum morifolium*", Euphytica, 29:525–530.

Gosling, ed., 1979, "The Chrysanthemum Manual—6th edition", The National Chrysanthemum Society, Essex Telegraph Press, London, pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and Rose Mutations Induced by X-rays", Am. Soc. Hort. Sci. Proc., pp. 613–620.

Broertjes, 1966, "Mutation Breeding of Chrysanthemums", Euphytica, 15:156–162.

Dowrick, et al., 1966, "The Induction of Mutations in Chrysanthemum Using X- and Gamma Radiation", Euphytica, 15:204–210.

*Primary Examiner*—Howard J. Locker
*Attorney, Agent, or Firm*—Foley & Lardner

[57] ABSTRACT

A Chrysanthemum plant named Foxy Valerie particularly characterized by its flat capitulum form; decorative capitulum type; dark red to greyed-purple ray floret color; diameter across face of capitulum of 35 to 44 mm when fully opened; branching pattern is spreading and prolific, with 6 to 9 laterals developing after pinch when grown outside under natural daylength in fall flowerings; natural season flower date of September 2 to 7 when planting rooted cuttings on June 17 to 21 in Salinas, Calif., and of October 7 to 14 when planting rooted cuttings June 15 to 18 in Hightstown, N.J.; plant height of 25 to 30 cm when grown in fall under natural daylength with no growth regulators; and durable, uniform performance.

1 Drawing Sheet

The present invention comprises a new and distinct cultivar of Chrysanthemum, botanically known as *Dendranthema grandiflora*, and referred to by the cultivar name Foxy Valerie.

Foxy Valerie, identified as 7988 (90-857B01), is a product of a mutation induction program. The new cultivar was discovered and selected by inventor Leon Glicenstein on Sep. 1, 1993 in a controlled environment in Salinas, Calif. as one flowering plant within a flowering block established as rooted cuttings from stock plants which had been exposed as unrooted cuttings to an X-ray source of 1750 rads in Fort Myers, Fla. on Feb. 11, 1993. The irradiated parent cultivar was the cultivar Valerie, disclosed in U.S. Plant Pat. No. 8,985 and described as a flat decorative garden mum with dark red-purple flower color.

The irradiation program resulting in Foxy Valerie had as its primary objective the expansion of color ranges of the parent cultivar. The irradiation program comprised irradiation of cuttings of the parent cultivar at irradiation levels of 1500, 1750 and 2000 rads. A total of 643 cuttings harvested from a total of 225 irradiated plants were planted on Jun. 21, 1993. Of these, 11 initial selections were made, which selections were then revegetated and reflowered. Three consecutive flowerings resulted in discarding 3 selections on Apr. 18, 1994. The 8 remaining selections were maintained as PIs (Possible Introductions) and were further trialed in Salinas, Calif., Hightstown, N.J. and Leamington, Ontario, Canada, ultimately resulting in discarding 5 of the selections on Oct. 17, 1994, and the decision to introduce one selection as Foxy Valerie. The two remaining selections were discarded on Oct. 13, 1995.

The first act of asexual reproduction of Foxy Valerie was accomplished when vegetative cuttings were taken from the initial selection in November of 1993 in a controlled environment in Salinas, Calif., by technicians working under supervision of Leon Glicenstein.

Horticultural examination of controlled flowerings of successive plantings has shown that the unique combination of characteristics as herein disclosed for Foxy Valerie are firmly fixed and are retained through successive generations of asexual reproduction.

Foxy Valerie has not been observed under all possible environmental conditions. The phenotype may vary significantly with variations in environment such as temperature, light intensity and daylength, without, however, any variance in genotype.

The following observations, measurements and comparisons describe plants grown in controlled open aread in Salinas, Calif., and in Hightstown, N.J. Rooted cuttings were established in soil and maintained outdoors under the natural temperature and daylength prevailing during June through October.

The following traits have been repeatedly observed and are determined to be basic characteristics of Foxy Valerie, which, in combination, distinguish this Chrysanthemum as a new and distinct cultivar:

1. Flat capitulum form.
2. Decorative capitulum type.
3. Dark red to greyed-purple ray floret color.
4. Diameter across face of capitulum of 35 to 44 mm when fully opened.

5. Branching pattern is spreading and prolific, with 6 to 9 laterals developing after pinch when grown outside under natural daylength in fall flowerings.

6. Natural season flower date of September 2 to 7 when planting rooted cuttings on June 7 to 21 in Salinas, Calif., and of October 7 to 14 when planting rooted cuttings June 15 to 18 in Hightstown, N.J.

7. Plant height of 25 to 30 cm when grown in fall under natural daylength with no growth regulators.

8. Durable, uniform performance.

The accompanying photographic drawing is a color photograph of Foxy Valerie grown as a pinched garden mum under natural season outside conditions in Salinas, Calif., with the colors being as nearly true as possible with illustrations of this type. Plants were grown outside and dug and transplanted in 15 cm pots for photography purposes.

Of the commercial cultivars known to the inventor, the most similar in comparison to Foxy Valerie is the parent cultivar Valerie. All traits of Foxy Valerie are similar to those of Valerie, except for the ray floret color. The ray floret color of Foxy Valerie is dark red (R.H.S. 46A), overlaid with greyed-purple (R.H.S. 187B), while the ray floret color of Valerie is described as dark red-purple (R.H.S. 61A to 61B).

In the following description color references are made to The Royal Horticultural Society Colour Chart. The color values were determined on plant material grown as a pinched garden mum grown outdoors in Salinas, Calif. on Sep. 8, 1995.

Classification:

*Botanical.*—*Dendranthema grandiflora* cv Foxy Valerie.

*Commercial.*—Flat decorative garden mum.

INFLORESCENCE

A. Capitulum:

*Form.*—Flat.

*Type.*—Decorative.

*Diameter across face.*—35 to 44 mm when fully opened.

B. Corolla of ray florets:

*Color (general tonality from a distance of three meters)*.—Dark red to greyed-purple.

*Color (upper surface)*.—46A, overlaid with 187B.

*Color (under surface)*.—187C.

*Shape.* natural daylength in fall flowerings.

B. Foliage:

*Color (upper surface)*.—147A.

*Color (under surface)*.—147B.

*Shape.*—Small, deeply lobed, serrated.

What is claimed is:

1. A new and distinct Chrysanthemum plant named Foxy Valerie, as described and illustrated.

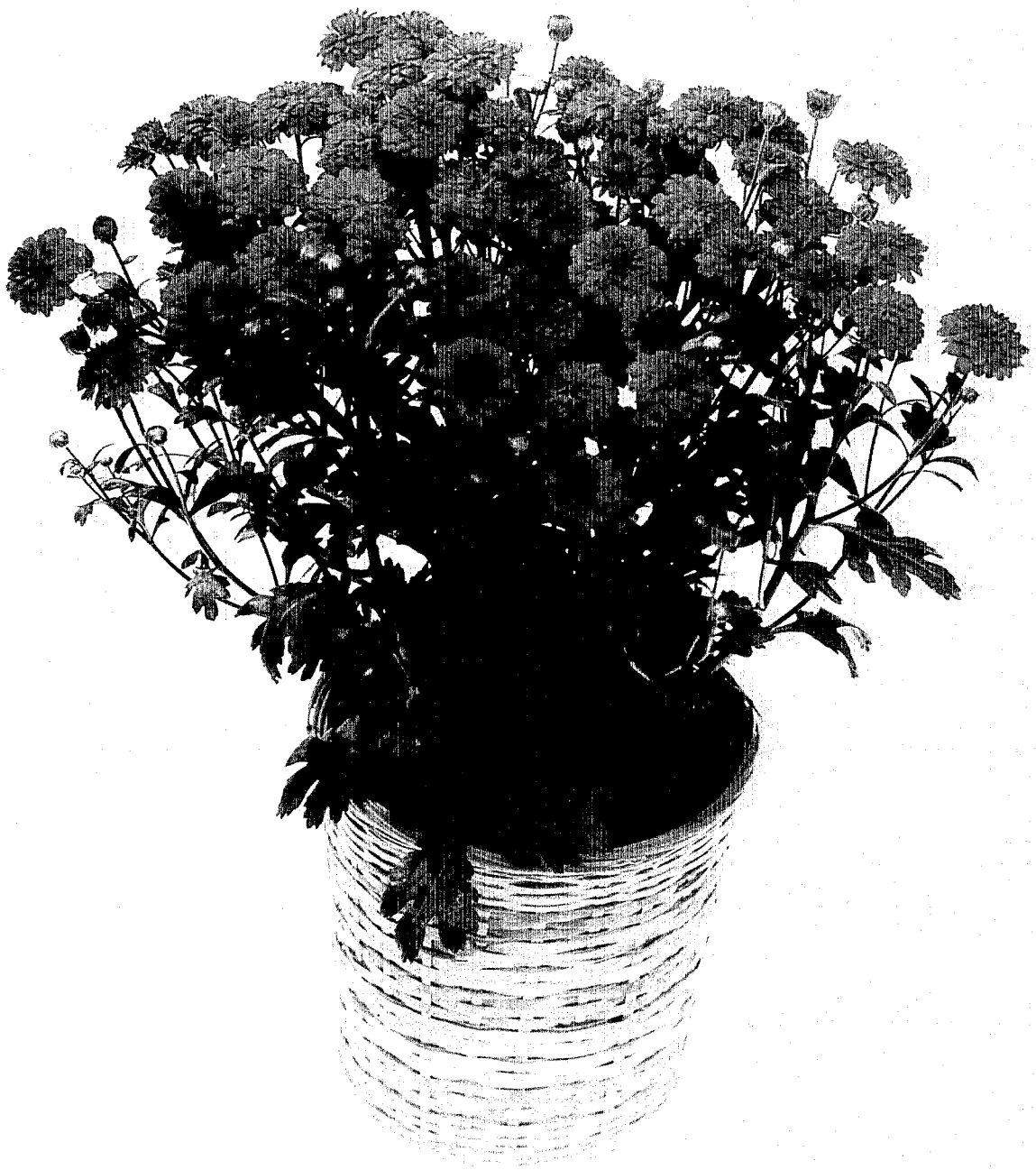

* * * * *